United States Patent
Sigg et al.

(10) Patent No.: US 8,119,148 B2
(45) Date of Patent: Feb. 21, 2012

(54) SUSPENSION COMPRISING OXCARBAZEPINE

(75) Inventors: Juergen Sigg, Loerrach (DE); Michael Billington, Riehen (CH)

(73) Assignee: Novartis Pharmaceuticals Corporation, East Hanover, NJ (US)

( * ) Notice: Subject to any disclaimer, the term of this patent is extended or adjusted under 35 U.S.C. 154(b) by 0 days.

(21) Appl. No.: 10/168,248

(22) PCT Filed: Dec. 19, 2000

(86) PCT No.: PCT/EP00/12968
§ 371 (c)(1),
(2), (4) Date: Jun. 18, 2002

(87) PCT Pub. No.: WO01/45671
PCT Pub. Date: Jun. 28, 2001

(65) Prior Publication Data
US 2003/0004155 A1    Jan. 2, 2003

(30) Foreign Application Priority Data
Dec. 20, 1999  (GB) .................................. 9930058.4

(51) Int. Cl.
*A61K 8/02*    (2006.01)
(52) U.S. Cl. ........................................ 424/401
(58) Field of Classification Search .................. 424/401
See application file for complete search history.

(56) References Cited

U.S. PATENT DOCUMENTS

| | | | |
|---|---|---|---|
| 3,716,640 A | | 2/1973 | Schindler |
| 4,004,029 A | * | 1/1977 | Collins et al. .................. 514/619 |
| 4,409,212 A | | 10/1983 | Mondadori |
| 4,427,681 A | | 1/1984 | Munshi |
| 4,431,641 A | * | 2/1984 | Mondadori et al. .......... 514/217 |
| 4,693,901 A | | 9/1987 | Hullah et al. |
| 4,996,222 A | | 2/1991 | Carlin |
| 5,032,393 A | | 7/1991 | Douglas |
| 5,122,543 A | * | 6/1992 | Khanna ...................... 514/772.5 |
| 5,409,907 A | | 4/1995 | Blase |
| 5,472,714 A | * | 12/1995 | Bourquin ...................... 424/472 |
| 5,607,707 A | * | 3/1997 | Ford et al. .......................... 426/2 |
| 5,631,323 A | * | 5/1997 | Guntherberg et al. .......... 525/71 |
| 5,646,131 A | * | 7/1997 | Badwan et al. .................. 514/58 |
| 5,660,861 A | * | 8/1997 | Jao et al. ........................ 424/465 |
| 5,686,104 A | * | 11/1997 | Mills et al. .................... 424/451 |
| 5,830,907 A | | 11/1998 | Doble et al. |
| 6,037,380 A | * | 3/2000 | Venables et al. ............. 514/781 |
| 6,146,876 A | * | 11/2000 | Robison et al. .............. 435/243 |

FOREIGN PATENT DOCUMENTS

| | | | |
|---|---|---|---|
| BO | RO81639 | * | 6/1983 |
| EP | 0 289 977 A | | 11/1988 |
| EP | 0765664 | | 4/1997 |
| EP | 0 843 998 | | 11/1997 |
| EP | 0 810 216 A | | 12/1997 |
| EP | 0751129 | | 11/1998 |
| FR | 2702148 A1 | | 9/1994 |
| FR | 2702149 A1 | | 9/1994 |
| FR | 2702151 A1 | | 9/1994 |
| GB | 9930058.4 | * | 12/1999 |
| JP | 60204713 | | 10/1985 |
| JP | 2178224 | | 7/1990 |
| JP | 6504991 | | 6/1994 |
| JP | 9110697 | | 4/1997 |
| JP | 10511640 | | 11/1998 |
| WO | WO 88 00825 A1 | | 2/1988 |
| WO | WO 92/12712 | | 8/1992 |
| WO | 9413298 | | 6/1994 |
| WO | WO 96/11687 | | 4/1996 |

OTHER PUBLICATIONS

Schicht, S., Wigger, D., Frey, H., "Pharmacokinetics of oxcarbazepine in the dog," 1996, J. Vet. Pharmacol. Therap., 19, 27-31, 1996.*
Schicht et al in "Pharmacokinetics of oxcarbazepine in the dog" J. Vet. Pharmacol. Therap, 1996, 19, pp. 27-31.*
Grant et al in "Oxcarbazepine: A review of its pharmacology and therapeutic potential in epilepsy, trigeminal neuralgia and affective disorders" Drugs 43(6), 1992, p. 873-888.*
Schicht S. et al., "Pharmacokinetics of oxcarbazepine in the dog," Journal of Veterinary Pharmacology and Therapeutics, vol. 19(1), pp. 27-31 (1996).
Kibbe AH (Ed.), "Handbook of Pharmaceutical Excipients, 3rd Ed." 2000, American Pharmaceutical Association, Washington, Pharmaceutical Press, London, pp. 102-106 & Wheatley TA, "Cellulose, microcrystalline" paragaph '0018.
"Avicel RC-591 Microcrystalline Cellulose and Carboxymethylcellulose Sodium, NF, BP, Pharmaceutical Emulsions and Suspensions", FMC Corp. Technical Bulliten (2003).
Ansel, H., Pharmaceutical Dosage Forms and Drug Delivery Systems, 6th Ed., 2000, Chapter 7, pp. 281-316, Editorial Premier, San Paulo, Brazil.
Schachter, S., Oxcarbazepine: current status and clinical applications, Exp. Opin. Invest. Drugs, 1999, 8 (7):1103-1112, Ashley Publications.
Remington: The Science and Practice of Pharmacy, pp. 2323-2324, Spanish 19th edition, 1998.

* cited by examiner

*Primary Examiner* — Bethany Barham
(74) *Attorney, Agent, or Firm* — Montgomery, McCracken, Walker & Rhoads, LLP; David J. Roper

(57) ABSTRACT

This invention provides a pharmaceutical composition in the form of a suspension comprising oxcarbazepine.

39 Claims, No Drawings

SUSPENSION COMPRISING OXCARBAZEPINE

This is a 371 of International Application No. PCT/EP00/12968, filed Dec. 19, 2000.

This invention relates to oral suspension formulations of oxcarbazepine (Trileptal®).

Oxcarbazepine (10,11-Dihydro-10-oxo-5H-di-benz[b,f]azepine-5-carboxamide) is a known anticonvulsant useful in the treatment of seizures resulting from, for example, an epileptic attack. Its preparation is described, e.g., in the German patent 2,011,087.

Oral suspension forms of oxcarbazepine are known in the art. They have been developed to obtain an additional dosage form for, e.g., pediatric use and for patients having difficulties in swallowing tablets.

We have found that an unexpected high viscosity/thixotropy, e.g. high viscosity and insufficient flow behavior as well as a brownish discoloration appears in commercially available suspensions after long-term storage. The insufficient flow behavior becomes apparent in the form of "lumps" which could only be re-dispersed with difficulty by a very vigorous shaking. The brownish discoloration would be due to the formation of degradation products of ascorbic acid when added as an antioxidant.

After intensive testing we have surprisingly found that it is possible to manufacture an oral suspension form of oxcarbazepine having improved physico-chemical properties so that their use by patients, e.g., epileptic children or adults having difficulties in swallowing tablets, is highly facilitated.

The present invention relates in a first aspect to a stable and easily pourable pharmaceutical composition in the form of a suspension comprising oxcarbazepine and having, when shaken, a viscosity in the range of 5 to 52 mPa·s., e.g. 10 to 40 mPa·s or 10 to 30 mPa·s, e.g., 10 to 25 mPa·s.

Under "shaken" is to be understood shaken prior to use, e.g. by a patient, e.g. vigorously shaken, e.g. by hand, e.g. for 5 to 30 s.

The viscosity may be measured, e.g., by using a Haake VT 550 viscometer (Searle-principle). For example, a Spindle type NV is used and the shear rate is set to 1000 s$^{-1}$. The measuring temperature is 20° C. The sample is vigorously shaken, e.g., by hand, prior to filling into the measuring beaker. The measurement then is carried out directly after filling. The suspension may be stirred 5 minutes at 1000 s$^{-1}$ before a reading is taken.

In a further aspect the present invention relates to a pharmaceutical composition in the form of a suspension comprising oxcarbazepine and one or more cellulosic polymers or mixtures thereof, comprising, e.g., a mixture of carboxymethylcellulose, e.g., its sodium salt, and microcrystalline cellulose, said mixture being present in a range of 1.25 to 1.95 g/100 mL, e.g., 1.35 to 1.65 g/100 mL, e.g., 1.5 g/100 mL. Preferably the ratio of carboxymethyl cellulose to microcrystalline cellulose in the mixture is 1:5 to 1:12 e.g., 1:8 to 1:10. As a preferred mixture one may use dispersible cellulose, e.g. as known under the trade name Avicel® RC, e.g. Avicel® RC 591, commercially available from e.g. FMC Corporation, USA. Avicel® RC 591 shows the following characteristics: carboxymethylcellulose sodium content from about 8.3 to about 13.8%, viscosity from about 39 to 91 cps, loss on drying not more than 6%, heavy metals not more than 0.001%, pH from about 6 to about 8, residue on ignition not more than 5% (manufacturer information).

The suspension of the invention provides various advantages including an absence of "lumps" even after long storage when the composition is shaken for use, as well as a highly improved pourability. Moreover, such a composition is stable, e.g. up to 3 years, and well tolerated for oral administration.

In a preferred embodiment, the composition of the invention comprises an antioxidant. Antioxidants may be employed to protect oxcarbazepine from oxidative degradation. Antioxidants may be selected from any of those compounds known in the art, e.g., ascorbic acid, sodium pyrosulfite, glutathion, or sorbic acid. The type and amount of antioxidant employed may be determined according the general knowledge of the man skilled in the art and may depend, e.g., upon the concentration of oxcarbazepine employed. For example, the antioxidant, e.g., ascorbic acid, may be present in a range of 0.75 to 2 g/100 mL, e.g. 1 g/100 mL. Further, the amount and type of antioxidant is preferably selected so that it does not influence the dissociation of the cellulosic polymer(s) or their mixtures. Other suitable antioxidants than those previously mentioned may be used as long as this condition is fulfilled.

As an alternative to the use of antioxidant compounds, in order to reduce the likelihood of forming oxidative degradation products, the antioxidant effect can be achieved by displacing oxygen (air) from contact with the oxcarbazepine suspension. This is usually carried out by purging with, e.g. nitrogen or carbon dioxide, a container holding the suspension when being packaged. Nevertheless, even if care is taken to purge a filled container of air, in large volume oxcarbazepine suspensions, e.g. larger than 60 ml, more particularly about 250 ml, oxidative degradation products may be detected after only relatively short storage periods. In the case of low volume oral suspensions, e.g., about 100 ml or less of oxcarbazepine, by carefully purging a filled container with nitrogen or other inert gas the formation of oxidative degradation products may be avoided. When the formulations are carefully purged of oxygen, the dissolved oxygen content may be less than 2 mg/ml, e.g. 1 mg/ml or lower.

Even for large volume of oral suspensions of the invention the formation of oxidative degradation products may be surprisingly avoided by judiciously selecting the type and quantity of antioxidant as described above. This may be the case irrespective of whether the precaution is taken of purging the system of air.

The pH of the suspension of the invention is selected having regard to the properties, e.g. stability, of certain excipients. It has been found that a certain pH may promote the formation of oxidative degradation products, e.g., of the antioxidant, e.g., furfurals from ascorbic acid. For example, the pH of a suspension, e.g. containing ascorbic acid as antioxidant, may be adjusted so that it is in a range of pH 2 to 4, e.g., pH 2.7 to 3.7. This provides a suspension with a better stability.

In a further embodiment of the invention the suspension may comprise between 1 to 20 g/100 mL, e.g., 5 to 7 g/100 mL, e.g., 6 g/100 mL of oxcarbazepine which is preferably in the form of a micronized substance. The quantity of particles larger than 40 micrometers (μm) is limited to a maximum of 5% by weight and the median particle size by Fraunhofer diffraction is specified to be within 4-10 μm.

In a further aspect the present invention relates to a pharmaceutical composition in the form of a suspension comprising oxcarbazepine and less than 0.5 g/100 mL of hydroxyethyl cellulose (HEC), e.g., no HEC.

In a further aspect the present invention relates to a pharmaceutical composition in the form of a thixotropic oral suspension comprising 6 g/100 mL oxcarbazepine and having, when shaken, a viscosity in the range of 5 to 52 or 5 to 50 mPas, e.g., 10 to 40 mPa·s or 10 to 30 mPas., e.g., 10 to 25 mPas.

In a further aspect the present invention relates to a pharmaceutical composition in the form of a suspension comprising oxcarbazepine which is capable of freely flowing out of an orifice having a 3 mm diameter at a speed in the range of 0.3 to 4 ml/second, e.g., 0.4 to 3 ml/second.

The suspensions suitable for oral administration are aqueous-based. By "aqueous based" is meant a suspension comprising water, or water and a water-miscible organic solvent or solvents. When an organic co-solvent is employed it is preferred that it is used in amounts of 0.5 to 10 g/100 mL. Suitable solvents are those water-miscible solvents commonly used in the art, e.g., propylene glycol (1,2-propane diol), polyethylene glycol 300, polyethylene glycol 400 and ethanol. Such solvents may also be solvents for preservatives which may optionally be used in the suspension.

Oral suspensions according to the invention may contain other excipients commonly employed in oral suspensions in order to provide the required stability and therapeutic efficacy.

Excipients may include:
preservatives, e.g., propylparaben, methylparaben, sorbic acid;
wetting agents, e.g., polyethylene glycol stearates, e.g. polyethylene glycol 400 monostearate, e.g. as known and commercially available under the trade name Cremophor S9® from e.g. BASF, Germany, Poloxamer, Polysorbates;
sweeteners, e.g., saccharin sodium, sorbitol solution, e.g. non crystallizing sorbitol solution;
flavoring agents, e.g., yellow plum lemon aroma, e.g. as commercially available from international Flavors and Fragrances, France.

Solvents other than water, when required, and other reagents may be chosen from medical grade reagents and solvents well known in the art.

In so far as manufacturers of any excipients used in suspension formulations are not described herein, details of excipients of the invention are described in Fiedler's "Lexikon der Hilfstoffe", 4th Edition, ECV Aulendorf 1996 and "Handbook of Pharmaceutical Excipients" Wade and Weller Ed. (1994) the contents of which are hereby incorporated by reference.

A typical composition according to the invention comprises (% expressed in mass/volume):

| | |
|---|---|
| Oxcarbazepine, micronized, e.g. TRILEPTAL/AS, extra fine, | 1 to 20% |
| Avicel RC 591 | 0.1 to 1.9% |
| Methylparaben | 0.01 to 1% |
| Polyethylene glycol 400 monostearate | 0.01 to 1% |
| Propylene glycol (1,2-propanediol), dist. | 0.5 to 10% |
| Propylparaben | 0.005 to 0.5% |
| Saccharin sodium, cryst. | 0.005 to 0.5% |
| Sorbic acid | 0.005 to 0.5% |
| Sorbitol solution (non crystallizing) | 10 to 40% |
| Ascorbic acid | 0.1 to 10% |
| Water, purified | 40 to 85% |
| Yellow plum-lemon aroma | 0 to 15% |

With exception of the Yellow plum-lemon aroma and Polyethyleneglycol-400-monostearate all excipients are listed in USP/NF XXIII.

The formulations of the invention are useful for the known indications of the particular active agent incorporated therein, e.g. for their anti-convulsive action and may be used as monotherapy or adjunctive therapy in the control, prevention or treatment of seizures, e.g. primary generalized tonic-clonic seizures and partial seizures, with or without secondary generalization, e.g. resulting from the onset of epilepsy, status epilepticus, cerbro-vascular disorders, head injury and alcohol withdrawal.

The exact amounts of active agent and of the formulation to be administered depend on a number of factors, e.g. the condition to be treated, the desired duration and the rate of release of the active agent. For example, the amount of active agent required and the release rate thereof may be determined on the basis of known in vitro and in vivo techniques, determining how long a particular active agent concentration in the blood plasma remains at an acceptable level for a therapeutic effect.

Examples of doses are: For epilepsy, the oral suspension may be administered in children in a daily maintenance dose of 30 mg/kg/day. For example, a 5 ml single dose containing 300 mg of oxcarbazepine may be given up to 3 times a day. In adults a daily maintenance dose ranges between 600 and 1200 mg/day. For example, a 5 ml single dose containing 300 mg of oxcarbazepine may be given up to 4 times a day.

In another aspect of the invention there is provided a process of preparing an oral suspension as hereinabove defined.

The process may be carried out in a conventional manner used in the art of manufacturing oral suspensions, e.g., by mixing all components of the suspension in one batch.

The process of preparing a oral suspension may be carried out in an inert, e.g., stainless steel reactor vessel optionally under an inert atmosphere, e.g. nitrogen.

A process of manufacturing of a composition according to the invention may comprise the following steps:

As a preliminary step, a preservative solution (A) is prepared by mixing the solvent for the preservative, preferably heated at 40-45° C., with the preservatives and a dispersion (B) is prepared by mixing purified water, preferably heated at 45-55° C., or 40-50° C., with the wetting agent.

The bulk suspension is then prepared by mixing purified water with the cellulosic polymers, e.g., Avicel RC 591. The mixture obtained is then mixed with solution (A). A sweetener or agent for decreasing microbiological activity, e.g., sorbitol solution, may be added. To the resulting mixture dispersion (B) is added. The antioxidant, e.g., ascorbic acid, is then added, optionally with a flavoring agent, e.g., yellow plum lemon aroma, e.g. yellow plum lemon aroma 39K020 or 20F, and a further sweetener, e.g., saccharin sodium. Oxcarbazepine is added and the final mixture is stirred, e.g. vigorously stirred, or homogenised to obtain bulk oral suspension (C). By bubbling nitrogen in small bubbles through the dispersion and later extraction of residual nitrogen bubbles by evacuation the content of dissolved oxygen in the dispersion is reduced to a minimum.

The resultant oral suspension is preferably maintained under an inert atmosphere and is transferred to containers, e.g., bottles, optionally after re-suspension. The process for filling containers is discussed hereinbelow.

In a further aspect the present invention relates to a container having a fill volume of, e.g., from about 50 ml to about 300 ml comprising an oxcarbazepine suspension as previously described.

Containers may be chosen which are made of material which is non-reactive or substantially non-reactive with the oral suspension.

Glass containers may be used although it is preferred to use plastic containers. Plastic containers are preferred over glass containers as they are relatively light weight and non-breakable and thus more easily stored. This is particularly the case for large volume suspensions. Plastic containers may be principally composed of thermoplastic polymers. Plastic materials may additionally comprise additives, for example plasticisers, fillers, antioxidants, antistatic agents and other ingredients known in the art for specific purposes.

A primary concern of container systems is the protection they afford a solution against UV degradation. If desired, amber glass employing iron oxide or an opaque cover fitted over the container may afford the appropriate UV protection.

A wide range of container sizes may be employed. Container size may be conveniently categorised as Low-Volume, e.g., 100 ml or less and High-Volume, e.g., above 100 ml and typically 250 ml. In view of the relatively low solubility of oxcarbazepine in water, which has a solubility of 3.2 to 4.2 mg/ml at 25° C. and pH of 5.8 to 6.0, it is preferable to use a High-Volume oral suspension, e.g. above 100, more particularly 250 ml in order to have an effective amount of active agent in a single container.

Notwithstanding that it may be preferable to employ organic co-solvents in Low-Volume oral suspensions, the Low-Volume oral suspension offers the advantage of being easier to store and use. Furthermore, the containers used for Low-Volume oral suspensions have a smaller head space when filled which contains less oxygen (air) than the larger containers needed for High-Volume oral suspensions. Containers used in Low-Volume oral suspensions therefore are more easily purged of air, e.g. using nitrogen or other inert gases.

Containers for use in the storage of the oral suspensions according to the invention may be used to administer a multiple dose of active agent. The device used to convey the oral suspension from the container into the body of a patient may be any of the devices commonly used in the art to deliver therapeutic agents as oral suspensions from containers, such as High- or Low-Volume containers as aforementioned. Preferably containers according to the present invention comprise a dosing syringe adapted to fit to said container.

Although the contact time between the device and the oral suspension may usually be brief, it may nevertheless be intimate, and therefore compatibility with the oral suspension should be assured. Accordingly, the material of the device may be the same as the material of the container or may include other materials commonly used in such devices if short term contact therewith is acceptable.

The process of filling containers with the oral suspension should be carried out under optimal hygienic conditions according to procedures well known in the art. Preferably the process is carried out under laminar air flow conditions.

The oral suspensions according to the invention and packaged in containers as described above are stable to prolonged periods of storage.

In a further aspect the present invention relates to a method for the treatment of epilepsy, e.g. the prevention or treatment of primary generalized tonic-clonic seizures and partial seizures, with or without secondary generalization, which method comprises administering to a subject in need thereof a composition according to the invention.

In a further aspect the present invention relates to the use of a composition according to the invention in the treatment of epilepsy, e.g. in the prevention or treatment of primary generalized tonic-clonic seizures and partial seizures, with or without secondary generalization.

In yet a further aspect the present invention relates to the use of a composition according to the invention in the manufacture of a medicament for the prevention or treatment of primary generalized tonic-clonic seizures and partial seizures, with or without secondary generalization.

EXAMPLES

Example 1

Preparation of an Oxcarbazepine Oral Suspension

A preservative solution (A) is prepared by mixing 2.5 g of propylene glycol, previously heated at 40-45° C., with 0.12 g of methylparaben, 0.03 g of propylparaben and 0.5 g of sorbic acid. A dispersion (B) is then prepared by mixing 0.5 to 50 g of purified water, previously heated at 45-55° C., with 0.1 g of polyethylene glycol 400 monostearate. The bulk suspension is then prepared by mixing the rest of purified water (to reach 71.70 g in total) with Avicel RC 591. The mixture obtained is then mixed with solution (A). 25 g of sorbitol solution (non crystallizing) is added. To the resulting mixture then dispersion (B) is added. Then ascorbic acid is added together with yellow plum lemon aroma and saccharin sodium. Oxcarbazepine is added and the final mixture is vigorously stirred to obtain the bulk oral suspension (C). By bubbling nitrogen in small bubbles through the dispersion and later extraction of residual nitrogen bubbles by evacuation the content of dissolved oxygen in the dispersion is reduced to below 2 mg/L. The resultant oral suspension has, when shaken, a viscosity of 15 mPa·s.

The resultant oral suspension is preferably maintained under an inert atmosphere and is transferred to containers, e.g., bottles, optionally after resuspension according to the process for filling containers discussed above.

Example 2

Composition of the Suspension

| | |
|---|---|
| Oxcarbazepine, micronized | 6.00 g |
| Avicel RC 591 | 1.50 g |
| Methylparaben | 0.12 g |
| Polyethylene glycol 400 monostearate | 0.10 g |
| Propylene glycol (1,2-propanediol), dist. | 2.50 g |
| Propylparaben | 0.03 g |
| Saccharin sodium, cryst. | 0.05 g |
| Sorbic acid | 0.05 g |
| Sorbitol solution (non crystallizing) | 25.00 g |
| Ascorbic acid | 1.00 g |
| Water, purified | 71.70 g |
| Yellow plum-lemon aroma 39K020 | 0.25 g |
| | 108.30 g (=100 ml) |

Example 3

Composition of a Suspension

| | |
|---|---|
| TRILEPTAL/AS, extra fine | 6.00 g |
| Avicel RC 591 | 1.50 g |
| Methylparaben | 0.12 g |
| Polyethylene glycol 400 stearate | 0.10 g |
| Propylene glycol (1,2-propanediol), dist. | 2.50 g |
| Propylparaben | 0.03 g |
| Saccharin sodium, cryst. | 0.05 g |
| Sorbic acid | 0.05 g |
| Sorbitol solution | 25.00 g |
| Vitamin C | 1.00 g |
| Water, purified | 71.70 g |
| Yellow plum-lemon aroma 20 F | 0.25 g |
| | 108.30 g (=100 ml) |

The invention claimed is:

1. A pharmaceutical composition in the form of a suspension comprising oxcarbazepine in an amount of 5 to 7 g/100 mL, an antioxidant, a mixture of carboxymethylcellulose and microcrystalline cellulose in a range of 1.25 to 1.95 g/100 mL, and 0 g/100 mL of hydroxyethylcellulose.

2. The composition according to claim 1 wherein the ratio of carboxymethylcellulose to microcrystalline cellulose in the mixture is 1:5 to 1:12.

3. The composition according to claim 1 wherein the carboxymethylcellulose in the mixture is a sodium salt.

4. The composition according to claim 1 wherein the antioxidant is ascorbic acid.

5. The composition according to claim 1 wherein the antioxidant is present in a range of 0.75 to 2 g/100 mL.

6. The composition according to claim 4 wherein the antioxidant is present in a range of 0.75 to 2 g/100 mL.

7. The composition according to claim 1 having a pH in the range of 2 to 4.

8. A container having a fill volume of from about 50 ml to about 300 ml comprising an oxcarbazepine suspension according to claim 1 and a dosing syringe adapted to fit said container.

9. A method for the treatment of primary generalized tonic-clonic seizures and partial seizures, with or without secondary generalization, which method comprises administering to a subject in need thereof a composition according to claim 1.

10. The composition according to claim 1 comprising oxcarbazepine in an amount of 6 g/100 mL.

11. The composition according to claim 1 wherein the mixture of carboxymethylcellulose and microcrystalline cellulose is present in an amount of 1.35 to 1.65 g/100 mL.

12. The composition according to claim 11 wherein the mixture of carboxymethylcellulose and microcrystalline cellulose is present in an amount of 1.5 g/100 mL.

13. The composition according to claim 1 wherein the ratio of carboxymethylcellulose to microcrystalline cellulose in the mixture is 1:8 to 1:10.

14. The composition according to claim 1 having a pH in the range of 2.7 to 3.7.

15. A pharmaceutical composition in the form of a suspension comprising oxcarbazepine in an amount of 5 to 7 g/100 mL, ascorbic acid, a mixture of carboxymethylcellulose and microcrystalline cellulose in a range of 1.25 to 1.95 g/100 mL, and 0 g/100 mL of hydroxyethylcellulose, and having a pH in the range of 2 to 4.

16. The composition according to claim 15 wherein the ratio of carboxymethylcellulose to microcrystalline cellulose in the mixture is 1:5 to 1:12.

17. The composition according to claim 15 wherein the carboxymethylcellulose in the mixture is a sodium salt.

18. A container having a fill volume of from about 50 ml to about 300 ml comprising an oxcarbazepine suspension according to claim 15 and a dosing syringe adapted to fit said container.

19. A method for the treatment of primary generalized tonic-clonic seizures and partial seizures, with or without secondary generalization, which method comprises administering to a subject in need thereof a composition according to claim 15.

20. The composition according to claim 15 comprising oxcarbazepine in an amount of 6 g/100 mL.

21. The composition according to claim 15 wherein the mixture of carboxymethylcellulose and microcrystalline cellulose is present in an amount of 1.35 to 1.65 g/100 mL.

22. The composition according to claim 21 wherein the mixture of carboxymethylcellulose and microcrystalline cellulose is present in an amount of 1.5 g/100 mL.

23. The composition according to claim 15 wherein the ratio of carboxymethylcellulose to microcrystalline cellulose in the mixture is 1:8 to 1:10.

24. The composition according to claim 15 having a pH in the range of 2.7 to 3.7.

25. The composition according to claim 24 wherein the ascorbic acid is present in a range of 0.75 to 2 g/100 mL.

26. A pharmaceutical composition in the form of a suspension consisting essentially of:
   oxcarbazepine in an amount of 1 to 20 g/100 mL;
   water;
   optionally at least one water-miscible organic co-solvent in an amount of 0.5 to 10 g/100 mL;
   ascorbic acid;
   a mixture of carboxymethylcellulose and microcrystalline cellulose in a range of 1.25 to 1.95 g/100 mL;
   optionally at least one preservative;
   optionally at least one wetting agent;
   optionally at least one sweetener;
   optionally at least one flavoring agent;
   wherein the composition has a pH in the range of 2 to 4.

27. The composition according to claim 26 wherein the ascorbic acid is present in a range of 0.75 to 2 g/100 mL and which has a pH in the range of 2.7 to 3.7.

28. The composition according to claim 27 wherein the oxcarbazepine is in an amount of 5 to 7 g/100 mL.

29. The composition according to claim 26 wherein there is said at least one water-miscible organic co-solvent in an amount of 0.5 to 10 g/100 mL.

30. The composition according to claim 26 wherein the ratio of carboxymethylcellulose to microcrystalline cellulose in the mixture is 1:5 to 1:12.

31. The composition according to claim 26 wherein the carboxymethylcellulose in the mixture is a sodium salt.

32. The composition according to claim 26 wherein the antioxidant is present in a range of 0.75 to 2 g/100 mL.

33. A container having a fill volume of from about 50 ml to about 300 ml comprising an oxcarbazepine suspension according to claim 26 and a dosing syringe adapted to fit said container.

34. A method for the treatment of primary generalized tonic-clonic seizures and partial seizures, with or without secondary generalization, which method comprises administering to a subject in need thereof a composition according to claim 26.

35. The composition according to claim 26 comprising oxcarbazepine in an amount of 6 g/100 mL.

36. The composition according to claim 26 wherein the mixture of carboxymethylcellulose and microcrystalline cellulose is present in an amount of 1.35 to 1.65 g/100 mL.

37. The composition according to claim 11 wherein the mixture of carboxymethylcellulose and microcrystalline cellulose is present in an amount of 1.5 g/100 mL.

38. The composition according to claim 26 wherein the ratio of carboxymethylcellulose to microcrystalline cellulose in the mixture is 1:8 to 1:10.

39. The composition according to claim 26 having a pH in the range of 2.7 to 3.7.

* * * * *